(12) United States Patent
Jacobsen et al.

(10) Patent No.: US 6,478,778 B1
(45) Date of Patent: Nov. 12, 2002

(54) APPARATUS FOR DELIVERING FLUIDS TO BLOOD VESSELS, BODY CAVITIES, AND THE LIKE

(75) Inventors: Stephen C. Jacobsen, Salt Lake City, UT (US); John Lippert, Park City, UT (US); Clark C. Davis, Salt Lake City, UT (US)

(73) Assignee: Precision Vascular Systems, Inc., West Valley City, UT (US)

( * ) Notice: Subject to any disclaimer, the term of this patent is extended or adjusted under 35 U.S.C. 154(b) by 0 days.

(21) Appl. No.: 09/321,973

(22) Filed: May 28, 1999

(51) Int. Cl.[7] ................................................ A61M 5/178
(52) U.S. Cl. ................................................ 604/167.01
(58) Field of Search .................... 604/96.01, 103.01, 604/103.03, 103.08, 93.01, 164.11, 167.01, 264, 523, 526, 530, 532, 507, 508; 424/423

(56) References Cited

U.S. PATENT DOCUMENTS

| | | |
|---|---|---|
| 4,935,004 A | 6/1990 | Cruz |
| 4,950,258 A | 8/1990 | Kawai et al. |
| 5,112,305 A | 5/1992 | Barath et al. |
| 5,354,279 A | 10/1994 | Höfling |
| 5,364,356 A | 11/1994 | Höfling |
| 5,554,114 A * | 9/1996 | Wallace et al. ............. 604/508 |
| 5,681,281 A | 10/1997 | Vigil et al. |
| 5,709,874 A * | 1/1998 | Hanson et al. ............. 424/423 |
| 5,873,865 A | 2/1999 | Horzewski et al. |
| 6,053,900 A | 4/2000 | Brown et al. |

* cited by examiner

Primary Examiner—Anhtuan T. Nguyen
Assistant Examiner—Michael M Thompson
(74) Attorney, Agent, or Firm—Snell & Wilmer, LLP

(57) ABSTRACT

Apparatus for delivering fluids to blood vessels, body cavities and the like, includes a resilient tubular wire for threading lengthwise into the lumen of a catheter and out the distal end thereof to a target location of a body passageway to be treated. The tubular wire has a central lumen and a distal end formed into a coil, which, when straightened, may be threaded lengthwise through the catheter, but when extended out the distal end of the catheter at the target location, resumes its coiled shape. The tubular wire includes openings at least on the outside of the coils for discharging radially outwardly medication carried in the lumen of the wire. In this manner, the medication may be directed toward the wall of the passageway to infuse a diseased area being treated.

2 Claims, 2 Drawing Sheets

APPARATUS FOR DELIVERING FLUIDS TO BLOOD VESSELS, BODY CAVITIES, AND THE LIKE

BACKGROUND OF THE INVENTION

1. Field of the Invention

This invention relates to invasive medical devices for delivering medications and therapeutic agents into blood vessels, body cavities, organs, tumors and the like. More particularly, the present invention relates to devices for concentrating the delivery of such medications and agents to the walls of the blood vessels and cavities.

2. State of the Art

Various vascular diseases involving vessel walls, for example, arterial sclerosis, aneurysm or other weakening of the vessel wall, occlusive lesions, etc., may benefit from the application of medications to the affected area of the vessel wall. This may be done systemically by injecting medication into the vessel and then allowing the blood to carry the medication to the affected area. The problem with this approach is that high dosages of medication are required to ensure that some small portion reaches the affected area, and the high dosage may be harmful to other organs or body parts. This approach is also expensive and not especially effective. Another approach to treating diseases of vessel walls is to place a block before and after the affected area and then inject medications into that portion of the vessel between the two blocks. The problem with this approach is that blood flow is stopped for a certain amount of time and this, in itself, is dangerous; also, it generally cannot be stopped long enough for effective uptake of the medication by the vessel walls.

Another prior art approach is to thread a catheter through the blood vessel to the affected area and then either supply the medication through the catheter to the affected area or supply the medication through a needle which itself is threaded through the catheter, pierce the vessel wall with the needle, and then supply the medication (see U.S. Pat. No. 5,354,279).

An additional prior art approach to supplying medication to a vessel wall involves the use of an inflatable sleeve positioned adjacent the affected area, where the sleeve includes an annular cavity holding the medication. When the sleeve is inflated to expand outwardly, the medication held in the cavity is placed into contact with the vessel walls and released thereinto. The problem with this approach is that the blood vessel again is blocked for a time and thus a gradual therapeutic regimen is not possible. Other approaches to delivering medication to vessel walls are disclosed in U.S. Pat. Nos. 5,681,281, 5,364,356, and 5,112,305.

It would therefore be desirable to have a device for delivering medication, therapeutic agents, and the like efficiently and effectively to a blood vessel wall, body cavity wall, etc. which is non-occlusive and substantially non-inhibiting of blood flow. It would also be desirable to have such a device which delivers medication substantially directly to a vessel wall, and may do so for an extended period of time.

OBJECTS AND SUMMARY OF THE INVENTION

It is therefore an object of the invention to provide a device for delivering medication, therapeutic agents, and the like efficiently and effectively to a blood vessel wall, body cavity wall, etc.

It is also an object of the invention to provide such a device which is non-occlusive and substantially non-inhibiting of blood flow.

It is another object of the invention to provide such a device which may be easily deployed through the vascular system and other body cavities to desired target locations for delivering the medication, therapeutic agents, and the like.

It is also an object of the invention to provide such a device which is capable of delivering medication substantially directly to a vessel or cavity wall.

It is still another object of the invention to provide such a device, in accordance with one aspect thereof, in which the degree to which blood or other cavity fluid mixes with the medication during administration may be controlled.

The above and other objects are realized in one illustrative embodiment of the invention which includes a resilient tubular wire for threading into a blood vessel or other body passageway to a target wall location which is to be treated with medication or other therapeutic agent. The tubular wire forms a coil at its distal end, and is configured for straightening and threading lengthwise into, through and out the terminal end of a catheter to the target wall location. The wire resumes the coil shape within the blood vessel or body cavity when its distal end exits the terminal end of the catheter. The wire includes a plurality of cuts or openings at least on the outside of the coils for discharging radially outwardly medication carried in the hollow of the wire. Discharge would occur once the coil was in place at the target location by supplying medication through the proximal end of the tubular wire. An occlusive coating formed, for example, by dip coating could be disposed over the wire and openings and then cuts selectively made in the coating to further control discharge of the medication.

In accordance with one aspect of the invention, rather than use a tubular wire, a solid wire could be used, again, having a coil shape at its distal end. A plurality of vesicles would be formed on the outside of the coils for holding fluid or dissolvable solids to be delivered toward the vessel or cavity walls. A sheath or membrane may be disposed over the coil wire to cover the vesicles. Such a membrane may be dissolvable in blood or body cavity fluid to release the contents of the vesicles or the membrane may be made of a permeable material through which the medication could pass.

In accordance with another aspect of the invention, the spacing between adjacent coils may be selectively varied to either increase the mixing of blood or body cavity fluid with the medication (adjacent coils separated some distance), or decrease the mixing (little or no distance between adjacent coils).

In accordance with yet another aspect of the invention, the coiled portion of the tubular wire may be coated with a soft coating of foam, fuzz, or hydrogel to provide a better seal between adjacent wires in the coil and between the coil and the wall of the body passageway. This coating further reduces mixing of the medication and bodily fluids within the passageway.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE PREFERRED EMBODIMENT

Figure 1:
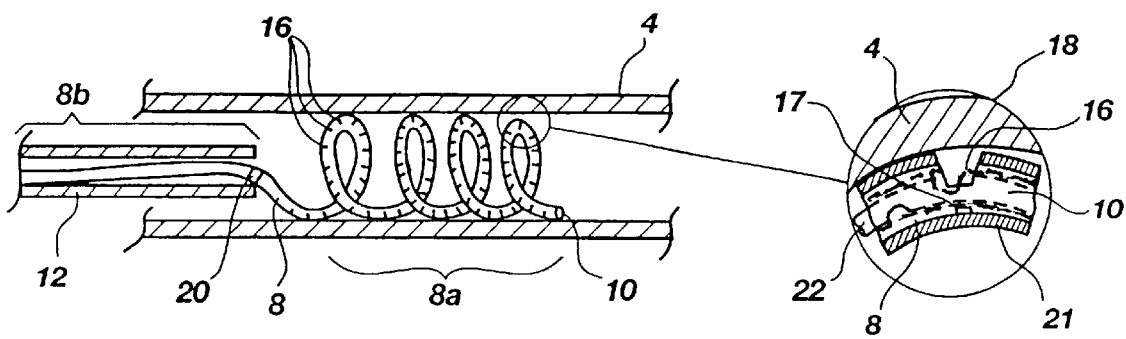
FIG. 1 is a side, partially cross-sectional view of a tubular wire fluid delivery device made in accordance with the principles of the present invention.

Referring to FIG. 1, there is shown a side, cross-sectional view the walls of a blood vessel 4 into which has been deployed the coil portion 8a of a tubular wire 8 having a central lumen 10. A non-coil portion 8b of the wire 8 is shown threaded in a catheter 12 which, itself, is shown threaded into the blood vessel 4. The tubular wire shown in FIG. 1 and subsequent figures is round in cross section. However, it will be apparent that tubular wires of other cross sectional shapes may also be used, and because of their different shape and structural properties may provide distinct advantages in certain circumstances. For example, the cross section of the tubular wire 8 may be round, square, hexagonal, octagonal, rectangular, oval, eliptical, or any other desired shape.

The coil portion 8a is initially straightened and inserted lengthwise into the catheter 12 for delivery to the target location in the blood vessel 4, but once the coil portion emerges from the distal end of the catheter, it resumes its coil shape. The threading of catheters into blood vessels and other body cavities, and the threading of wires or other treatment objects through catheters are well known to those skilled in the art.

The coil portion 8a of the tubular wire 8 is formed with a plurality of cuts or openings 16 on the outside of the coils so that at least when the portion 8a is unconstrained to resume the coil shape, the cuts 16 open additionally to allow flow of fluid medications, therapeutic agents, etc from the central lumen 10. Cuts 16 may also be provided on the inside of the coils as well, to help determine the shape and flexibility of the wire 8. (see enlarged section of wire at 18). However, it will be apparent that these inside cuts will preferably not communicate with the central lumen 10 of the wire 8 because any openings on the inside of the coils will tend to provide medication toward the inside of the coil, which is not desired. Otherwise, some or all of the inward cuts should preferably be sealed with an occlusive coating to prevent inward flow of the medication.

The cuts or openings 16, whether on the inside or outside of the coil, may be formed non-uniform in size, shape, or spacing so as to vary the flexibility and stiffness of the wire 8. It will be apparent to those skilled in the art that the shape, size, and spacing of cuts formed on an elongate member will have a direct effect on the ultimate shape, flexibility, and stiffness of the member. For example, widely spaced openings 16 will make the wire 8 less flexible than more closely spaced openings. Similarly, deeper or wider openings 16 will make the wire 8 more flexible. Thus, where a tighter coil is desired, the cuts may be placed closer together, or made deeper or wider, and where it is desired that the coil have a larger diameter, the cuts or openings may be made shallower or at a greater spacing.

It will also be apparent that the geometry of the cuts on the inside of the coil, if any, will preferably vary from that of the cuts or openings on the outside of the coil. As noted above, the cuts on the inside of the coil preferably are not as deep as the cuts on the outside of the coil, and do not communicate with the lumen 10 of the tubular wire. Thus, the spacing, size, and shape, of the cuts or openings may be non-uniform between the outside and inside of the coil, as well as varying along the length of the tubular wire.

Since cuts or openings 16 which communicate with the lumen 10 of the tubular wire are formed on the outside of the coils, when medication is transmitted through the lumen 10 of the tubular wire 8 and out the openings 16, the medication is caused to flow radially outwardly toward the walls of the blood vessel 4. In this manner, medication can be delivered directly toward a diseased portion of the wall of the blood vessel 4 to better infuse the diseased portion with the medication. Of course, if the coil portion 8a has been dimensioned to press outwardly against the walls of the blood vessel 4, any medication emerging from the openings 16 would come in direct contact with the wall.

Preferably, the tubular wire 8 is made of nickel-titanium alloy, but may also be made of various polymers, stainless steel, composites, or other suitable materials and combinations of these. The cuts or openings 16 are preferably made by saw cutting or grinding (see co-pending U.S. patent application, Ser. No. 08/714,555, filed Sep. 16, 1996, now issued as U.S. Pat. No. 6,014,919, such as with an abrasive blade, but may also be formed by chemical etching, laser cutting, electro-discharge machining (EDM) or other method suitable for making micro cuts or openings. The preferred saw cutting method uses a micromachining process which allows very accurate longitudinal, depth, width, and angular position control of the cuts on the very fine tubular wire. This method has been found to be superior to other methods in controlling the quality and consistency of cuts, and is also far more economical than other methods, such as EDM.

In use, the catheter 12 is threaded through the blood vessel 4 until the distal end of the catheter reaches a target location in the blood vessel to be treated. Then, the tubular wire 8 is threaded through the lumen of the catheter 12 and out the distal end thereof to enable the coil portion 8a to resume the coil shape. The medication may be supplied through the lumen 10 of the tubular wire 8 to exit the cuts or openings 16 and thereby treat the diseased portion of the blood vessel 4.

After delivery of the medication, the tubular wire 8 may then be retracted back through the catheter 12. Alternatively, the tubular wire 8 could include a discontinuity 20 which, when mechanically stressed, would cause severance at the location of the discontinuity. By this means, the substantially linear proximal portion of the tubular wire 8 may be advantageously detached from the distal coiled portion 8a so as to leave it in place in the blood vessel 4 to act as a stent to maintain the blood vessel patency (see co-pending U.S. patent application, Ser. No. 09/023,806, filed Feb. 13, 1998), now issued as U.S. Pat. No. 6,022,369. The entire disclosure of U.S. Pat. No. 6,022,369 is hereby incorporated by reference.

A polyurethane or similar plastic coating 21 (shown in the enlarged view 18 of FIG. 1) may be applied to selected parts of the coil portion 8a to better control the outflow of medication through the openings 16. For example, if only one side of the vessel wall were to be treated, a polyurethane coating could be applied to all but those portions of the coils which were to be in contact or adjacent to the side of the blood vessel wall to be treated. The coating 21 will block the exit of medication from the openings 16 which are covered, while allowing the exit of medication through openings that are not covered. Alternatively, the entire coil portion 8a could be covered with a plastic coating (for example, by dip coating), and then cuts made selectively in the coating, to allow discharge of medication from the tubular wire 8 only from selected locations along the tubular wire.

Another approach to controlling release of medication through the openings 16 in the tubular wire 8 would be to include in the lumen 10 of the tubular wire 8 an inner liner 22 (shown in the enlarged view 18 of FIG. 1) which itself has very small perforations (or porosity) selectively positioned along its length to control the medication discharge, for example, to provide more uniform distribution of medication discharge along the coil portion 8a. The liner material might illustratively be polysulfone.

Figure 2:
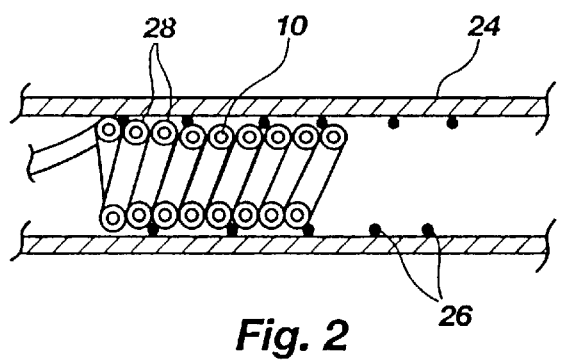
FIG. 2 is a side, partially cross-sectional view of the device of the present invention shown in place in a blood vessel within a stented vessel or duct.

FIG. 2 shows a side, partially cross-sectional view of a blood vessel 24 in which is disposed a conventional stent 26 for holding the blood vessel or duct open. Shown disposed within the conventional stent 26 is the coil portion of a tubular wire 28 through which medication is to be delivered to the walls of the blood vessel 24. Note that the coils of the coil portion of the tubular wire 28 are in intimate contact with one another so that medication released toward the walls of the blood vessel 24 cannot be greatly diluted by blood flowing through the coil interior of the tubular wire. Rather, the tight coil configuration of the tubular wire 28 tends to hold the medication between the exterior of the coil and the vessel walls to better medicate the target locations of the blood vessel being treated. The presence of the regular stent 26 may also inhibit the flow of blood adjacent to the blood vessel walls and this further inhibits dilution of the medication.

Figure 3:
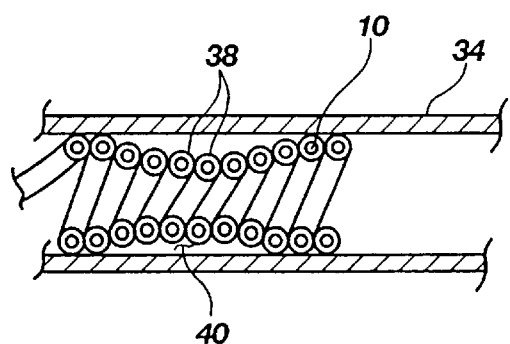
FIG. 3 is a side, partially cross-sectional view of an hourglass coil configuration of the present invention in which adjacent coils are in contact with one another.

FIG. 3 is a side, partially cross-sectional view of a blood vessel 34 in which is disposed the coil portion of a tubular wire 38, with the coil portion having an hourglass shape as shown. The coils located at the ends of the coil portion have a greater diameter and are in contact with the walls of the blood vessel 34 while the coils located centrally are smaller in diameter and are out of contact with the walls, to define an annular space 40 between the coils of the tubular wire 38 and the walls of the blood vessel. The medication is released into this annular space 40 to contact the walls of the blood vessel 34, with little interference from blood flowing in the blood vessel. In particular, the combination of adjacent coils of the tubular wire 38 being in contact with one another and the end most coils of the coil portion contacting the walls of the blood vessel 34, work to stagnate fluid located in the annular space 40 so that medication released into the space is not washed away.

Figure 4:
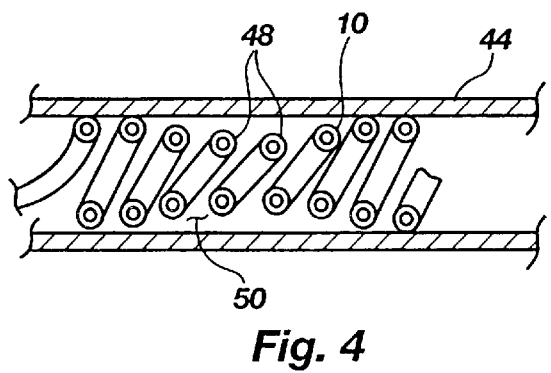
FIG. 4 is a side, partially cross-sectional view of an hourglass coil configuration of the present invention in which adjacent coils are spaced apart.

FIG. 4 shows a similar hourglass configuration of the coil portion of a tubular wire 48 (as in FIG. 3), but here the adjacent coils are spaced apart so that the annular space 50 is less isolated and protected from the flow of blood in the blood vessel 44. In this configuration, of course, more blood would mix with the medication and dilute it. By controlling the spacing between adjacent coils of the coil portion of the tubular wire 48, the amount of mixing of the released medication and blood can be controlled.

Figure 5:
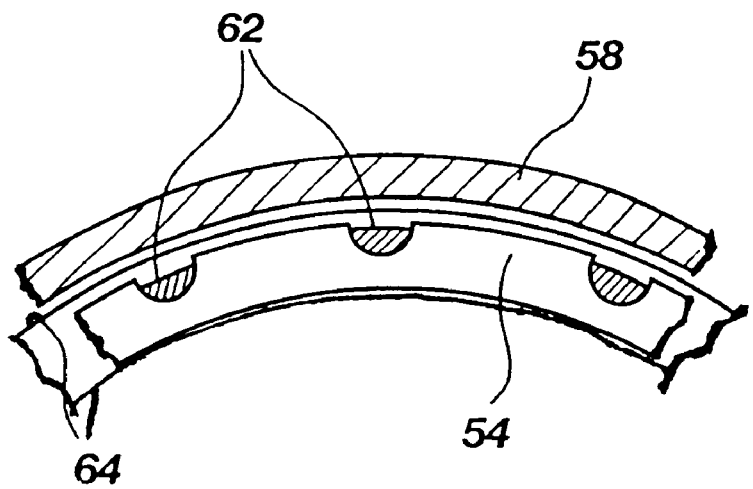
FIG. 5 is a side, cross-sectional view of a solid-wire embodiment of the present invention.

FIG. 5 shows an alternative embodiment, in cross-sectional view, of a solid wire 54 delivery device, shown disposed against a vessel or cavity wall 58. Formed on the side of the wire 54 adjacent the wall 58 are a plurality of vesicles or cavities 62 in which fluid medication, pellets, capsules, or similar medicaments are disposed. By positioning the wire 54 tightly against the wall 58, the medication in the vesicle 62 migrates therefrom to the vessel wall.

Advantageously, a membrane or sheath 64 is disposed about the wire 54 (formed, for example, by dip coating) to hold the medication in place in the vesicles 62 until the wire is deployed to the desired target location. The sheath 64 may be made of a blood dissolvable material such as polyvinyl alcohol or a permeable material such as polysulfone, to allow the discharge of the medication from the vesicles either upon dissolution of the sheath or through the sheath, as the case may be.

Figure 6:
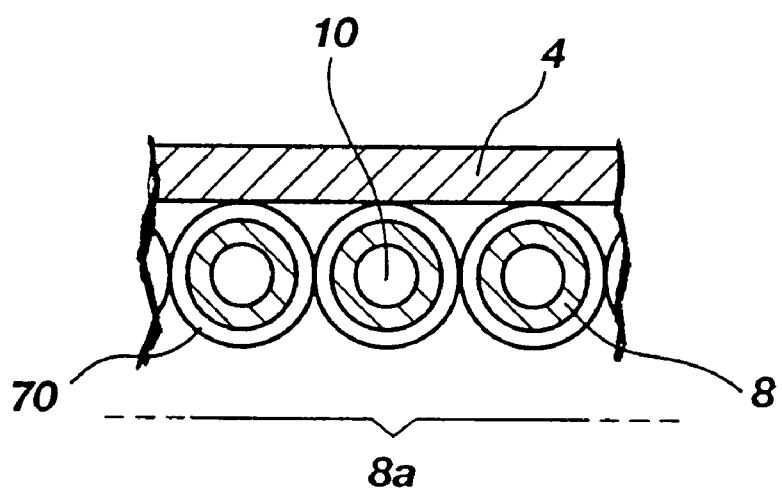
FIG. 6 is a side, partially cross-sectional view of a portion of the fluid delivery device of the present invention in which the outer surface of the wire is coated with a thin layer of fuzz, foam, or hydrogel.

Shown in FIG. 6 is yet another alternative embodiment of the fluid delivery device of the present invention. FIG. 6 provides a side, partially cross-sectional view of a portion of the coil section 8a of the tubular wire 8 disposed against the inner surface of a blood vessel wall 4. In this embodiment, the wire 8 having lumen 10 is advantageously coated on its outside with a thin coating 70 of fuzz, foam, or hydrogel to help prevent mixing of blood or other bodily fluids with the therapeutic fluid being delivered. This layer 70 of soft fuzz, foam, or hydrogel provides an improved seal between adjacent coils, and between the coils and the vessel wall 4. With this embodiment, the therapeutic fluid may be more completely isolated from the surrounding bodily fluids, and prevented from mixing therewith, thus improving the efficacy of treatment and reducing the required dosage. It will be apparent that this coating 70 may be included with several of the previous embodiments of the invention as described above.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An apparatus for delivering medication to a wall of a body cavity, said apparatus comprising:

a resilient tubular wire having a central hollow, at least a portion of said wire being resiliently formed into a coil having an outside surface at the wire's distal end, a proximal portion of said wire comprising a linear shape, and means for detaching the distal coil portion of the wire from the proximal portion of the wire, said tubular wire being configured to be straightened for threading lengthwise through a catheter, and to resume its coiled shape when extended beyond the distal end of the catheter to a target location; and said wire including a plurality of openings formed at least on the outside of the coil, at least some of said openings communicating between the outer surface and the central hollow of said tubular wire for discharging radially outwardly medication carried in the central hollow of the wire, to thereby direct medication toward the wall of the cavity.

2. An apparatus for delivering medication to a wall of a body cavity, said apparatus comprising:

a resilient tubular wire having a central hollow, at least a portion of said wire being resiliently formed into a coil having an outside surface, said tubular wire being configured to be straightened for threading lengthwise through a catheter, and to resume its coiled shape when extended beyond the distal end of the catheter to a target location, said wire including a plurality of openings formed at least on the outside of the coil, at least some of said openings communicating between the outer surface and the central hollow of said tubular wire; and an inner liner disposed in the hollow of the tubular wire, said liner including a plurality of perforations selectively positioned to control exit of medication carried in the central hollow of the wire through the openings in the tubular wire.

* * * * *